(12) United States Patent
Gribkov

(10) Patent No.: US 10,040,745 B2
(45) Date of Patent: Aug. 7, 2018

(54) PROCESS FOR THE PREPARATION OF 1-(3,5-DICHLOROPHENYL)-2,2,2-TRIFLUOROETHANONE AND DERIVATIVES THEREOF

(71) Applicant: SYNGENTA PARTICIPATIONS AG, Basel (CH)

(72) Inventor: Denis Gribkov, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/515,271

(22) PCT Filed: Oct. 7, 2015

(86) PCT No.: PCT/EP2015/073118
§ 371 (c)(1),
(2) Date: Mar. 29, 2017

(87) PCT Pub. No.: WO2016/058881
PCT Pub. Date: Apr. 21, 2016

(65) Prior Publication Data
US 2017/0217865 A1 Aug. 3, 2017

(30) Foreign Application Priority Data
Oct. 14, 2014 (EP) .................................. 14188744

(51) Int. Cl.
*C07C 45/46* (2006.01)
*C07C 45/63* (2006.01)
(Continued)

(52) U.S. Cl.
CPC .............. *C07C 45/63* (2013.01); *C07C 45/46* (2013.01); *C07C 201/08* (2013.01); *C07C 201/12* (2013.01); *C07C 205/45* (2013.01)

(58) Field of Classification Search
CPC ....... C07C 45/46; C07C 45/63; C07C 201/12; C07C 205/45
See application file for complete search history.

(56) References Cited

FOREIGN PATENT DOCUMENTS

| CN | 101177379 A | 5/2008 |
|----|-------------|--------|
| CN | 101377862 A | 1/2009 |

(Continued)

OTHER PUBLICATIONS

International Search Report for PCT/EP2015/073118, dated Dec. 15, 2015.
(Continued)

*Primary Examiner* — Sikarl A Witherspoon

(57) ABSTRACT

A process for the preparation of a compound of formula (I) wherein $R_1$ is hydrogen, fluoro or chloro; which process comprises: a) reacting a compound of formula (II) wherein $R_1$ is hydrogen, fluoro or chloro; with a nitration agent to the compound of formula (III) wherein $R_1$ is hydrogen, fluoro or chloro; b) reacting the compound of formula (III) with trichloroisocyanuric acid in the presence of sulfuric acid or fuming sulfuric acid to the compound of formula (IV) wherein R1 is hydrogen, fluoro or chloro; and c) reacting the compound of formula (III) with chlorine gas at a temperature from 180° C. to 250° C. to the compound of formula (I).

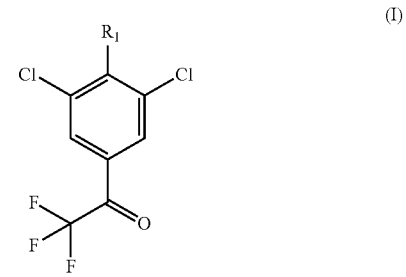

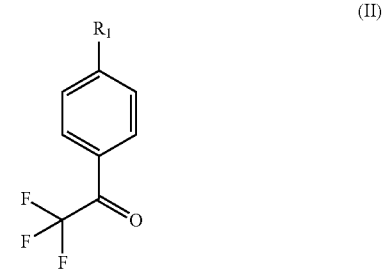

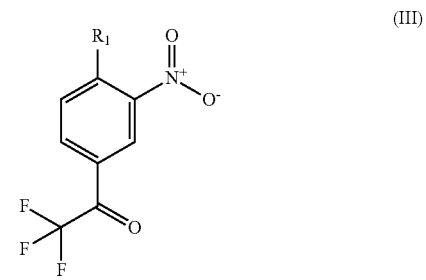

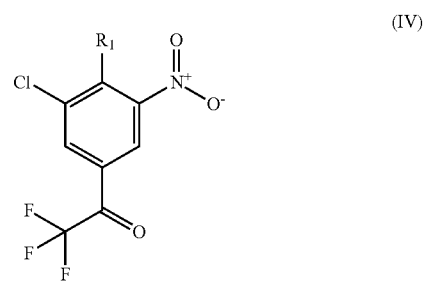

4 Claims, No Drawings

(51) Int. Cl.
  *C07C 201/00*  (2006.01)
  *C07C 205/00*  (2006.01)
  *C07C 201/08*  (2006.01)
  *C07C 201/12*  (2006.01)
  *C07C 205/45*  (2006.01)

(56) References Cited

FOREIGN PATENT DOCUMENTS

CN    103664511 A    3/2014
WO    2012120135 A1  9/2012

OTHER PUBLICATIONS

Hua Cai et al: "Lithium Binaphtholate-Catalyzed Enantioselective Enyne Addition to Ketones: Access to Enynylated Tertiary Alcohols", The Journal of Organic Chemistry, vol. 79, No. 12, Jun. 20, 2014 (Jun. 20, 2014), pp. 5484-5493, XP055170830.

Fonseca Mendona, Gabriela et al: "Trichloroisocyanuric acid in 98% sulfuric acid: A superelectrophilic medium for chlorination of deactivated arenes", Applied Catalysis A: General, vol. 401, No. 1, May 14, 2011 (May 14, 2011), pp. 176-181, XP028231781, Elsevier Science, Amsterdam, NL, ISSN: 0926-860X, DOI: 10.1016/J.APCATA.2011.05.017.

Stewart, Ross et al: "The Acidity of Some 1-5 Aromatic Fluoro Alcohols and Ketones", Canadian Journal of Chemistry, vol. 38, No. 3, Mar. 1, 1960 (Mar. 1, 1960), pp. 399-406, XP055170935, ISSN: 0008-4042.

Miller. Max W. et al: "Anti coccidial 1-5 derivatives of 6-azauracil. 3. Synthesis, high activity, and short plasma half-life of 1-phenyl-6-azauracils containing sulfonamide substituents", Journal of Medicinal Chemistry, val. 23, No. 10, Oct. 1, 1980 (Oct. 1, 1980), pp. 1083-1087, XP055170315, ISSN: 0022-2623, DOI: 10.1021/jm00184a005 scheme III, reaction 29 >30.

Database WPI 1-5, Week 199204 Thomson Scientific, London, GB; AN 1992-028871, XP002736195, JP H03 275646 A, Dec. 6, 1991 (Dec. 6, 1991) abstract.

Sott et al.: "Synthesis of dioxin-like monofluorinated PCBs: for the use as internal standards for PCB analysis", Tetrahedron, vol. 64, No. 18, Jan. 5, 2008 (Jan. 5, 2008), pp. 4135-4142, XP022551930, Elsevier Science Publishers, Amsterdam, NL ISSN: 0040-4020, DOI: 10.1016/J.TET.2008.01.003.

Atsuyoshi Ohno et al: "NAD (P)+-NAD (P)H Model. 46. Kinetic study on the reduction with a sulfur-containing NAD (P)H model", Tetrahedron Letters, vol. 24, No. 46, Jan. 1, 1983 (Jan. 1, 1983), pp. 5123-5126, XP055233744, GB ISSN: 0040-4039, DOI: 10.1016/S0040-4039 (00)94058-9.

Klabunde, Kenneth J. et al: "Amino-substituted .alpha., .alpha., .alpha.-trifluoroacetophen ones", The Journal of Organic Chemistry, vol. 35, No. 5, May 1, 1970 (May 1, 1970), pp. 1711-1712, XP055233821.

International Search Report and Written Opinion for PCT/EP2015/073118, dated Apr. 13, 2016.

PROCESS FOR THE PREPARATION OF 1-(3,5-DICHLOROPHENYL)-2,2,2-TRIFLUOROETHANONE AND DERIVATIVES THEREOF

RELATED APPLICATION INFORMATION

This application is a 371 of International Application No. PCT/EP2015/073118 filed Oct. 7, 2005, which claims priority to EP Application No. 14188744.8, filed Oct. 14, 2014, the contents of which are incorporated by reference herein.

The present invention relates to the preparation of halo-substituted 1-aryl-2,2,2-trifluoro-ethanones (compounds Ia, Ib and Ic):

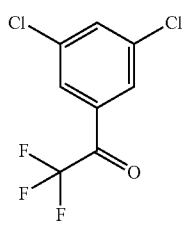
(Ia)

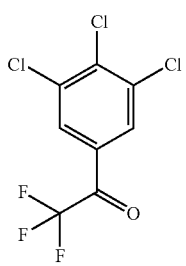
(Ib)

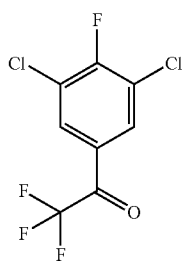
(Ic)

and to intermediates useful for said process. Said compounds are important intermediates for the preparation of pesticidally active isoxazoline-substituted benzamides as for example 1-(3,5-dichloro-4-fluoro-phenyl)-2,2,2-trifluoro-ethanone (Ic) disclosed in EP 1932836A1.

Typically said compounds of formula Ia, Ib and Ic are prepared by reaction of the corresponding organometallic reagents derived from halo-substituted 5-bromo-benzenes of formula VIa, VIb and VIc

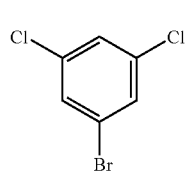
(VIa)

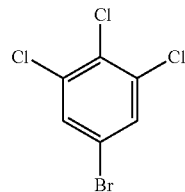
(VIb)

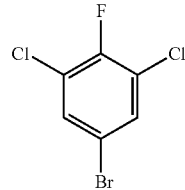
(VIc)

with the derivatives of trifluoroacetic acid (for example ethyl trifluoroacetate). For example the preparation of 2,2,2-trifluoro-1-(3,4,5-trichlorophenyl)ethanone (I b) is described in WO 2012/120135.

The corresponding bromo derivatives of the formula VIa, VIb and VIc are not easily available and prepared via multistep procedures. For example, 5-bromo-1,2,3-trichloro-benzene (VI b) can be prepared as described in Sott, R.; Hawner, C.; Johansen, J. E. Tetrahedron 2008, 64, 4135. 5-bromo-1,3-dichloro-2-fluoro-benzene (VI c) is especially difficult to prepare in particular on a large scale with the described synthesis being an inefficient multistep approach in Miller, M. W.; Mylari, B. L.; Howes, H. L.; Figdor, S. K.; Lynch, M. J.; Lynch, J. E.; Koch, R. C. J. Med. Chem. 1980, 23, 1083 but also in CN 101177379, CN 101337862 and CN 103664511 (Scheme 1).

Scheme 1

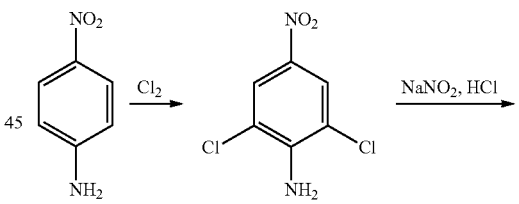

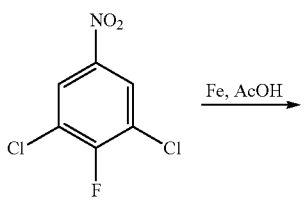

-continued

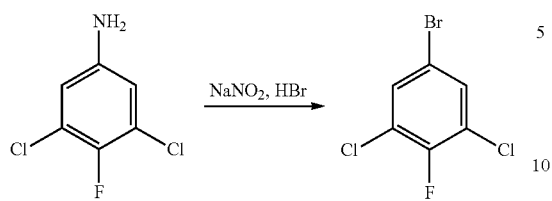

A significant disadvantage of these known processes is the low overall yields caused by the large number of reaction steps (4-6) and consequently high production cost. Moreover the synthesis generates large quantities of waste and has low atom economy.

It is therefore the object of the present invention to provide a process for the preparation of halo-substituted 1-aryl-2,2,2-trifluoro-ethanones with a reduced number of reaction steps, high yield and substantially lower production costs.

Thus, according to the present invention, there is provided a process for the preparation of a compound of formula I

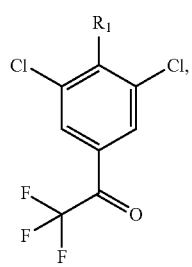

(I)

wherein $R_1$ is hydrogen, fluoro or chloro; which process comprises a) reacting a compound of formula II

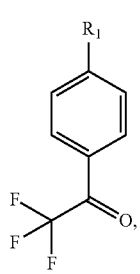

(II)

wherein $R_1$ is hydrogen, fluoro or chloro; with a nitration agent to the compound of formula III

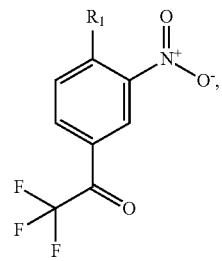

(III)

wherein $R_1$ is hydrogen, fluoro or chloro;

b) reacting the compound of formula III with trichloroisocyanuric acid in the presence of sulfuric acid or fuming sulfuric acid to the compound of formula IV

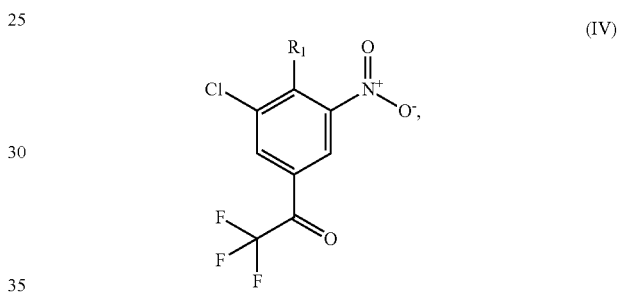

(IV)

wherein $R_1$ is hydrogen, fluoro or chloro; and c) reacting the compound of formula IV with chlorine gas at a temperature from 180° C. to 250° C. to the compound of formula I.

Reaction Step a):

Compounds of formula II are commercially available and several methods are reported in the literature for their preparation. For example, compounds of formula II, wherein $R_1$ is hydrogen or chloro, can be easily synthesized in high yields via Friedel-Crafts acylation of benzene and chlorobenzene respectively with trifluoroacetyl chloride or trifluoroacetic anhydride in the presence of a Lewis acid catalyst (aluminium chloride). However, the preparation of a compound of formula II, wherein $R_1$ is fluoro, via Friedel-Crafts method is only reported in a single publication using expensive 1-(trifluoroacetyl)-4-(dimethylamino)pyridinium trifluoroacetate as an acylating agent.

It was surprisingly found that the compound of formula II wherein $R_1$ is fluoro, can be synthesized in analogy to the synthesis of compound of formula II wherein $R_1$ is chloro, using trifluoroacetyl chloride in the presence of aluminium chloride in good yield. Therefore, the present invention also relates to a process for the preparation of a compound of formula II,

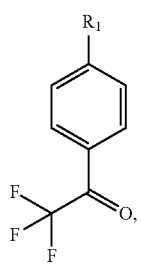

(II)

wherein $R_1$ is fluoro; characterized in that fluorobenzene is reacted with trifluoroacetyl chloride in the presence of aluminium chloride.

The compound of formula III, wherein $R_1$ is hydrogen, is known (CAS 1960-27-6) and can be prepared via nitration according to Canadian Journal of Chemistry, 1964, vol. 42, p. 439-446; and Canadian Journal of Chemistry, vol. 38, no. 3, pages 399-406, ISSN:0008-4042.

The compound of formula III, wherein $R_1$ is hydrogen, (CAS 657-15-8) is commercially available and can be prepared via nitration according to for example WO 2013/100632 A1. The compound of formula III, wherein $R_1$ is fluoro (CAS 1297553-45-7) is described for example in US 2011/130445 A1. The compound of formula III, wherein $R_1$ is chloro, is novel and was developed specifically for the preparation of the compounds of the formula I. Accordingly, said compound also form part of the subject-matter of the present invention.

The nitration of the compound of formula II can be performed using nitration agents like a mixture of concentrated sulfuric acid (4-6 equiv., concentrated or fuming) and concentrated or fuming nitric acid (1.02 to 1.1 equiv. 65%) without solvent at temperatures of 20° C. to 100° C. Instead of nitric acid, its sodium or potassium salts (sodium nitrate or potassium nitrate) can be also used. Also to minimize the sulfuric acid waste and to be able to perform the following step in the same pot, a combination of fuming sulfuric acid (20, 30 or 66% dissolved $SO_3$) and fuming nitric acid (90-100%) can be advantageously used. For example, fuming sulfuric acid with 30% $SO_3$ content in combination with 99% fuming nitric acid allows reducing the use rate of acid by 50% (2-3 equiv.).

Reaction Step b):

The chlorination of the compounds of formula III to the compounds of formula IV requires a very powerful electrophilic chlorinating agent due to intrinsic low reactivity of compounds III towards electrophilic substitution. This inertness is caused by the presence of 3 strong electron withdrawing groups (F, $NO_2$, and trifluorocarbonyl groups in the compound of formula III, wherein $R_1$ is fluoro). It was surprisingly found that the compounds of formula III can be chlorinated using commercially available and inexpensive trichloroisocyanuric acid in combination with concentrated or fuming sulfuric acid at high temperatures (80-160° C.). Trichloroisocyanuric acid is known to be a powerful chlorinating agent when combined with sulfuric acid, however no examples of chlorination of such deactivated substrates were reported. Merely the chlorination of 1,3-dinitrobenzene with trichloroisocyanuric acid in 98% sulfuric acid at 130° C. has been reported, though only 50% yield of the corresponding product was obtained. (Mendoca, G. F.; Senra, M. R., Esteves, P. M.; de Mattos, M. C. S. Applied Catalysis A: General, 2011, vol. 401, p. 176-181). Therefore, the success of this transformation was surprising.

Advantageously the transformation of the compound of formula III to the compound of formula IV can also be performed in a one-pot procedure, without isolation of the intermediate of formula III, since the reaction media ($H_2SO_4$) is the same for both reaction steps. The chlorinating agent is simply added portion-wise to the crude reaction mixture when the nitration is completed.

The compounds of formula IV

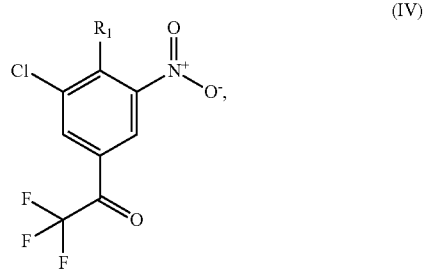

(IV)

wherein $R_1$ is hydrogen, fluoro or chloro; are novel and were developed specifically for the preparation of the compounds of the formula (I). Accordingly, they also form part of the subject-matter of the present invention.

Reaction Step c):

The substitution of an aromatic nitro group by a chlorine atom using chlorine gas at high temperatures (200° C.) is a well-known transformation. However, this transformation is only applicable to a special class of substrates which can tolerate such drastic conditions. There are no examples described in the prior art of this transformation on substrates having as a substituent a trifluoroacetyl group on the aromatic ring. The reaction is performed by passing chlorine gas through a neat compound of formula IV (no solvent) at temperatures from 180 to 250° C., preferably from 200 to 220° C. The product can be advantageously removed by distillation during the reaction. This also accelerates the conversion of the remaining starting material. A slight vacuum can be applied to facilitate the distillation. If the product cannot be efficiently removed by distillation during the course of the reaction, the unreacted starting material of formula IV can be separated from the product by fractional distillation afterwards and reused in the next run. The reaction mixture is highly corrosive.

According to EP 0163230A2 corrosion can be substantially reduced to acceptable levels by adding a small amount of HF/water-binding agents, for example anhydrous calcium chloride or silicon dioxide. In a preferred embodiment of the invention, small amount of anhydrous calcium chloride (1-5 mol %) are added to the reaction mixture in order to reduce corrosion of the glass surfaces.

PREPARATORY EXAMPLES

Example P1

Preparation of the compound of formula IIIb: 1-(4-chloro-3-nitro-phenyl)-2,2,2-trifluoro-ethanone

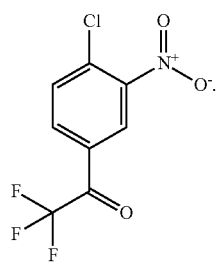

(IIIb)

In a 50 mL 3-neck round-bottom flask equipped with a magnetic stirrer, a thermometer and a dropping funnel, was placed fuming sulfuric acid (12.0 g, 20-30% $SO_3$). The flask content was cooled to 5° C. and compound of formula IIb (1-(4-chlorophenyl)-2,2,2-trifluoro-ethanone, 9.48 g, 45.0 mmol) was added in one portion. Fuming nitric acid (3.09 g, 48.6 mmol) was added to the mixture during 5 minutes. The temperature rose to 60° C. After the addition was complete, the cooling bath was removed and the reaction mixture was stirred at ambient temperature for 40 minutes. (At this point HPLC analysis indicated a complete conversion of the starting material to compound of formula IIIb). The reaction mixture was placed in an ice bath and water (1.4 g) was added to the mixture. The solution was extracted twice with dichloromethane (10 mL and 5 mL). The solvent was removed under vacuo to give the title compound of formula IIIb (1-(4-chloro-3-nitro-phenyl)-2,2,2-trifluoro-ethanone, 11.40 g). According to the quantitative $^1$H NMR analysis (1,1,2,2-tetrachloroethane as an internal standard) the material had purity of 97%.

$^1$H NMR (400 MHz, $CDCl_3$) δ ppm 7.82 (d, J=8.5 Hz, 1H), 8.21 (dm, J=8.6 Hz, 1H), 8.55 (d, J=1.8 Hz, 1H).

$^{13}$C NMR (101 MHz, $CDCl_3$) δ ppm 116.1 (q, $1J_{C-F}$=290.5 Hz), 126.9 (d, J=2.2 Hz), 129.1, 133.1, 133.5 (q, J=2.20 Hz), 134.6, 148.4, 177.9 (q, $2J_{C-F}$=36.6 Hz).

$^{19}$F NMR (376 MHz, $CDCl_3$) δ ppm −71.92.

Example P2

Preparation of the compound of formula IVb: 1-(3,4-dichloro-5-nitro-phenyl)-2,2,2-trifluoro-ethanone

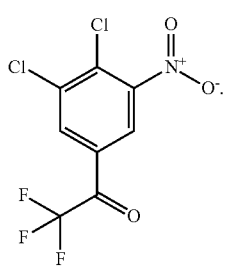

(IVb)

A 50 mL single-neck round-bottom flask equipped with a magnetic stirrer was charged with the compound of formula IIIb (1-(4-chloro-3-nitro-phenyl)-2,2,2-trifluoro-ethanone, 6.535 g, 25.0 mmol, 97% purity) and fuming sulfuric acid (10.0 g, 20-30% $SO_3$). The flask was placed in an oil bath and heated to 105° C. (external temperature). Trichloroisocyanuric acid (1.96 g, 8.4 mmol) was added in one portion. The reaction mixture was stirred for 1 h and 15 min followed by the addition of a second portion of trichloroisocyanuric acid (0.47 g, 2.0 mmol). After 2 h and 15 min of stirring, the conversion of the starting material was 96% (HPLC analysis, area % at 220 nm). A third portion of trichloroisocyanuric acid (0.2 g, 0.9 mmol) was added and the reaction was stirred overnight. The Next morning (14 h since the addition of the last portion of trichloroisocyanuric acid) the conversion was 100% and a small quantity of poly-chlorinated by-products was observed (<10 area %). The reaction mixture was allowed to cool to ambient temperature and water (1.6 g) was added while cooling in a water bath. The solution was extracted twice with dichloromethane (10 mL and 5 mL). The solvent was removed under vacuo to give the title compound of formula IVb (1-(3,4-dichloro-5-nitro-phenyl)-2,2,2-trifluoro-ethanone) as a pale yellow liquid (7.39 g). According to the quantitative $^1$H NMR analysis (1,1,2,2-tetrachloroethane as an internal standard) the material had purity of 88.5%.

The crude material was purified by fractional distillation at 0.07 mbar using a 10 cm Vigreux column to give 6.01 g of compound of formula IVb with chemical purity of 93% (quantitative $^1$H NMR analysis, 1,1,2,2-tetrachloroethane as an internal standard)

$^1$H NMR (400 MHz, $CDCl_3$) δ ppm 8.34 (d, J=0.8 Hz, 2H)

$^{13}$C NMR (101 MHz, $CDCl_3$) δ ppm 115.9 (q, $1J_{C-F}$=290.5 Hz), 124.0 (m), 129.0, 133.3, 133.8 (d, J=2.20 Hz), 137.3, 150.1, 177.2 (q, $2J_{C-F}$=37.3 Hz).

$^{19}$F NMR (376 MHz, $CDCl_3$) δ ppm −71.85.

Example P3

Preparation of the compound of formula Ib: 2,2,2-trifluoro-1-(3,4,5-trichlorophenyl)ethanone

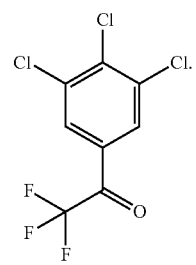

(Ib)

In a 10 mL 2-neck round-bottom flask equipped with a magnetic stirrer, a glass pipe for gas introduction and a reflux condenser, was placed a compound of formula IVb (1-(3,4-dichloro-5-nitro-phenyl)-2,2,2-trifluoro-ethanone, 5.82 g, 18.8 mmol, 93% purity). The flask was placed in an oil bath and heated to 220° C. (external temperature). A slow stream of chlorine gas was introduced under the liquid surface over a period of 9.5 h. Reaction off-gas was scrubbed into a 10% sodium hydroxide solution. After this time the conversion of the starting material was 99.5% (GC area %, FID). The reaction mixture was purged with nitrogen to remove the chlorine gas from the system and simultaneously cooled to about 60° C. Dichloromethane (5 mL) was introduced through the reflux condenser and the resulting solution was discharged. The flask was rinsed with a small quantity of dichloromethane (5 mL). The solvent was removed under vacuo to afford compound of formula Ib (2,2,2-trifluoro-1-(3,4,5-trichlorophenyl)ethanone) as white crystalline material (5.37 g). The title compound of formula Ic had chemical purity of 93% according to the quantitative $^1$H NMR analysis (1,1,2,2-tetrachloroethane as an internal standard).

$^1$H NMR (400 MHz, CDCl$_3$) δ ppm 8.05 (d, J=0.8 Hz, 2H)

$^{13}$C NMR (101 MHz, CDCl$_3$) δ ppm 116.1 (q, 1J$_{C-F}$=290.5 Hz), 129.0, 129.5 (m), 135.8, 139.5, 177.9 (q, 2J$_{C-F}$=36.6 Hz).

$^{19}$F NMR (376 MHz, CDCl$_3$) δ ppm −71.68.

Example P4

Preparation of the compound of formula Ic: 2,2,2-trifluoro-1-(4-fluorophenyl)ethanone

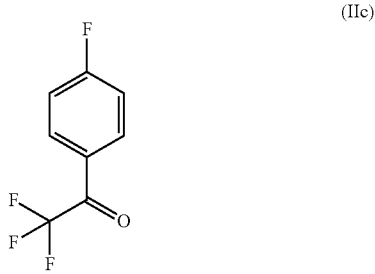 [SMILES: O=C(c1ccc(F)cc1)C(F)(F)F]

(IIc)

In a 2 L glass reactor equipped with a cooling circulator, a mechanical stirrer and a glass pipe for gas introduction, was placed fluorobenzene (865 g, 9.00 mol). The reactor's content was cooled to −5° C. and finely-powered anhydrous aluminum chloride (444 g, 3.30 mol) was added in one portion. A stream of trifluoroacetyl chloride gas (400 g, 3.02 mol) was introduced under the liquid surface over a period of 3 h at −5° C. (2.2 g/min). Reaction off-gas was scrubbed in a 10% sodium hydroxide solution. The reaction mixture was stirred for additional 3 h at 0° C. and then it was slowly added to ice-cold water (1200 g) while keeping the temperature below 30° C. (intensive cooling required). The aqueous lower layer was separated and the organic layer was washed with water (300 mL). The product was isolated by fractional distillation using 50 cm Vigreux column as follows: Most of fluorobenzene was distilled at normal pressure while increasing the bad temperature from 100 to 140° C. Then the bad temperature was reduced to 80° C. and the apparatus was evacuated to 200 mbar. After distilling remaining fluorobenzene the product was collected at the head temperature of 100-101° C. (200 mbar). Yield 437 g. According to the quantitative $^1$H NMR analysis (1,1,2,2-tetrachloroethane as an internal standard) the material had purity of 99%. The recovered fluorobenzene (546 g) was used in the next run.

AIs spectroscopic data were in agreement to those of commercially available material.

Example P5

Preparation of the compound of formula IIIc: 2,2,2-trifluoro-1-(4-fluoro-3-nitro-phenyl)ethanone

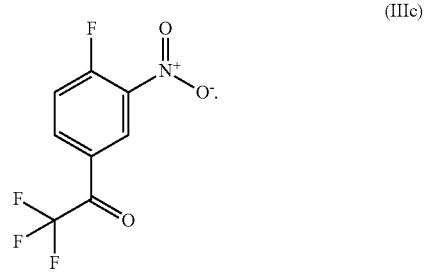

(IIIc)

In a 100 mL 3-neck round-bottom flask equipped with a magnetic stirrer, a thermometer and a dropping funnel was placed compound of formula IIc (2,2,2-trifluoro-1-(4-fluorophenyl)ethanone, 19.8 g, 102.0 mmol) and concentrated sulfuric acid (50.0 g, 95-98%, 492 mmol). Concentrated nitric acid (10.5 g, 65%, 107.1 mmol) was added over a period of 15 min. During the addition time, the reaction mixture was allowed to reach 55° C. and then it was kept at this temperature by cooling using a water bath. After the addition was completed, the water bath was removed and the reaction mixture was stirred overnight at ambient temperature (15 h). Water (13.0 g) was added to the reaction mixture. The pale yellow organic layer was separated and contained mostly the compound of formula IIIc. According to the quantitative $^1$H NMR analysis (1,1,2,2-tetrachloroethane as an internal standard) the material had purity of 95.6%.

$^1$H NMR (400 MHz, CDCl$_3$) δ ppm 7.55 (dd, J=9.8, 8.8 Hz, 1H), 8.38 (dm, J=8.9 Hz, 1H), 8.79 (dd, J=7.0, 2.0 Hz, 1H)

$^{13}$C NMR (101 MHz, CDCl$_3$) δ ppm 116.1 (q, 1J$_{C-F}$=290.5 Hz), 120.0 (d, J=21.7 Hz), 126.6 (d, J=4.1 Hz), 128.6, 136.8 (dm, J=10.5 Hz), 137.9, 159.3 (d, 1J$_{C-F}$=276.6 Hz), 177.6 (q, 2J$_{C-F}$=36.8 Hz)

$^{19}$F NMR (376 MHz, CDCl$_3$) δ ppm −104.95 (s, 1F), −71.78 (s, 3F).

Example P6

Preparation of the compound of formula IIIc: 2,2,2-trifluoro-1-(4-fluoro-3-nitro-phenyl)ethanone (using fuming nitric acid)

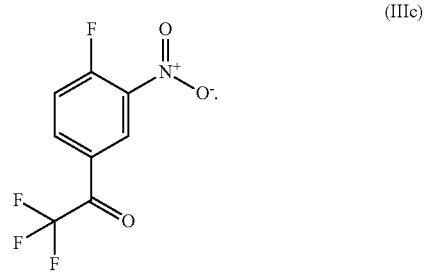

(IIIc)

In a 100 mL 3-neck round-bottom flask equipped with a magnetic stirrer, a thermometer and a dropping funnel was placed compound of formula IIc (2,2,2-trifluoro-1-(4-fluorophenyl)ethanone, 38.8 g, 200 mmol) and concentrated sulfuric acid (40.0 g, 95-98%, 400 mmol). Fuming nitric acid (13.9 g, 99%, 215 mmol) was added over a period of 1 h and 30 min. During the addition time, the reaction mixture was allowed to reach 60° C. After the addition was completed, the reaction mixture was stirred at 60° C. for 1 h. The pale yellow organic layer was separated to give 46.0 g of the title compound. According to the quantitative $^1$H NMR analysis (1,1,2,2-tetrachloroethane as an internal standard) the material had purity of 97.5%.

Example P7

Preparation of the compound of formula IVb: 1-(3-chloro-4-fluoro-5-nitro-phenyl)-2,2,2-trifluoro-ethanone (one pot reaction from compound IIc, 2,2,2-trifluoro-1-(4-fluorophenyl)ethanone)

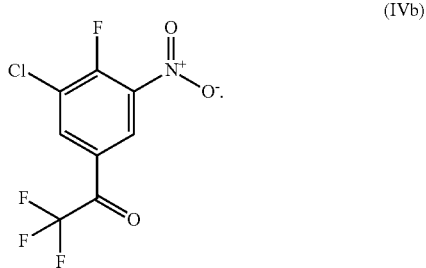

(IVb)

In a 50 mL 3-neck round-bottom flask equipped with a magnetic stirrer, a thermometer and a dropping funnel, was placed fuming sulfuric acid (20.4 g, 20-30% $SO_3$). The flask content was cooled to 5° C. in an ice bath and compound of formula IIc (2,2,2-trifluoro-1-(4-fluorophenyl)ethanone, 10.0 g, 51.5 mmol) was added in one portion. Fuming nitric acid (3.42 g, 54 mmol) was added to the mixture during 15 minutes while keeping the temperature below 25° C. The cooling bath was removed and the reaction mixture was stirred at ambient temperature for 1 h. At this point HPLC analysis indicated 99.4% conversion of starting material of formula IIc to the intermediate of formula IIIc. The flask was placed in an oil bath and heated to 120° C. (external temperature). Trichloroisocyanuric acid (4.00 g, 17.2 mmol) was added in one portion. The reaction mixture was stirred for 1 h and 20 min followed by the addition of a second portion of trichloroisocyanuric acid (1.05 g, 4.5 mmol). After 14 h of stirring, the conversion of the starting material was 75% (HPLC). A third portion of trichloroisocyanuric acid (0.97 g, 4.2 mmol) was added and the temperature was increased to 140° C. After stirring for an additional 6 h at 140° C., the conversion reached 94%. The reaction mixture was allowed to cool to ambient temperature and water (4.2 g) was slowly added while cooling in a water bath. The product was extracted twice with dichloromethane (10 mL and 5 mL). The solvent was removed under vacuo to give the title compound of formula IVb as yellow oily liquid (13.2 g). According to the quantitative $^1$H NMR analysis (1,1,2,2-tetrachloroethane as an internal standard) the material had purity of 88.0%.

The crude material of formula IVb from different experiments (47.6 g) was purified by fractional distillation at 0.07 mbar using a 25 cm Vigreux column to give compound of formula IVb (44.62 g, b. p. 58-61° C.) with chemical purity of 92% (quantitative $^1$H NMR analysis, 1,1,2,2-tetrachloroethane as an internal standard).

$^1$H NMR (400 MHz, CDCl$_3$) δ ppm 8.41 (dm, J=5.8 Hz, 1H), 8.65 (dm, J=6.0 Hz, 1H).

$^{19}$F NMR (376 MHz, CDCl$_3$) δ ppm −105.95 (s, 1F), −71.67 (s, 3F).

Example P8

Preparation of the compound of formula IVb: 1-(3-chloro-4-fluoro-5-nitro-phenyl)-2,2,2-trifluoro-ethanone (one pot reaction from compound IIc, 2,2,2-trifluoro-1-(4-fluorophenyl)ethanone, product isolation by distillation)

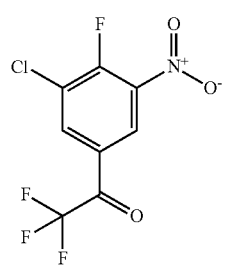

(IVb)

In a 0.5 L glass reactor equipped with a cooling circulator, a mechanical stirrer and two dropping funnels were placed compound of formula IIc (2,2,2-trifluoro-1-(4-fluorophenyl)ethanone, 194 g, 1.00 mol) and concentrated sulfuric acid (70.0 g, 95-98%, 0.70 mmol). Fuming sulfuric acid (66% $SO_3$, 127 g, 1.05 mol $SO_3$) and fuming nitric acid (99%, 66.8 g, 1.05 mol) were simultaneously added in 2 h while keeping the temperature below 50° C. The reaction mixture was stirred for 5 h at 25° C. and then 1 h at 50° C. Fuming sulfuric acid (66% $SO_3$, 150 g, 1.24 mol $SO_3$) was added to the reaction mixture in 1 h. The reaction mixture was heated to 100° C. followed by addition of trichloroisocyanuric acid (81 g, 0.33 mol) in several portions within 2 h at 100-105° C. The reaction mixture was stirred for 3 h and 30 min followed by the addition of trichloroisocyanuric acid (15.2 g, 0.062 mol) in one portion. After 3 h stirring at 100-105° C. a next portion of trichloroisocyanuric acid (7.7 g, 0.031 mol) was added and the temperature was increased to 120° C. Finally, after 4 h stirring at 120° C. a last portion of trichloroisocyanuric acid (7.7 g, 0.031 mol) and the stirring was continued for 2 h. At this time the conversion reached 99%.

The reaction mixture was cooled to ambient temperature and water (25 g) was slowly added. The product was isolated by distillation under reduced pressure over a 20 cm Vigreux column direct from the reaction mixture (b. p 97-100° C., 4 mbar). Yield 269 g. According to the quantitative $^1$H NMR

Example P9

Preparation of the compound of formula Ic, 1-(3,5-dichloro-4-fluoro-phenyl)-2,2,2-trifluoro-ethanone

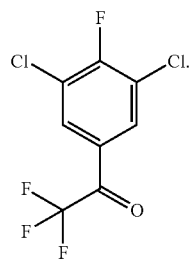

(Ic)

In a 100 mL 2-neck round-bottom flask equipped with a magnetic stirrer, a thermometer, a glass pipe for gas introduction and a reflux condenser, was placed the compound of formula IVc (1-(3-chloro-4-fluoro-5-nitro-phenyl)-2,2,2-trifluoro-ethanone, 10.0 g, 33.9 mmol, 92% purity). The flask was placed in an oil bath and heated to 230° C. (external temperature). A slow stream of chlorine gas was introduced under the liquid surface over a period of 18 h and 30 min. Reaction off-gas was scrubbed in a 10% sodium hydroxide solution. At this time, the conversion of the starting material was 71% according to $^1$H NMR analysis. The reaction mixture was cooled to ambient temperature and discharged. The crude reaction mixture was fractionated under vacuo (18 mbar) using a 10 cm Vigreux column to separate the title compound of formula Ic (b.p. 88-90° C., 6.25 g) from the starting material IVc (3.25 g, distillation residue). The title compound of formula Ic had a purity of 88% according to the quantitative $^1$H NMR analysis (1,1,2,2-tetrachloroethane as an internal standard). The distillation residue contained 81.5% of compound of formula IVc and 7.3% of compound of formula Ic.

Isolated yield of compound of formula Ic 62.2%.

Yield of the recovered starting material IVc 26.4%.

Compound of Formula Ic:

$^1$H NMR (400 MHz, CDCl3) δ ppm 8.05 (dd, J=6.1 Hz, 0.8 Hz, 2H).

$^{13}$C NMR (101 MHz, CDCl3) δ ppm −116.2 (q, $1J_{C\text{-}F}$=290.54 Hz), 124.1 (d, J=18.6 Hz), 126.8 (d, J=4.7 Hz), 131.0, 158.7 (d, $1J_{C\text{-}F}$=262.7 Hz), 177.6 (q, $2J_{C\text{-}F}$=37.08 Hz).

$^{19}$F NMR (376 MHz, CDCl3) δ ppm −102.51 (s, 1F), −71.56 (s, 3F).

analysis (1,1,2,2-tetrachloroethane as an internal standard) the material had purity of 91.5%.

Example P10

Preparation of the compound of formula Ic, 1-(3,5-dichloro-4-fluoro-phenyl)-2,2,2-trifluoro-ethanone (large scale experiment; reaction in the presence of calcium chloride)

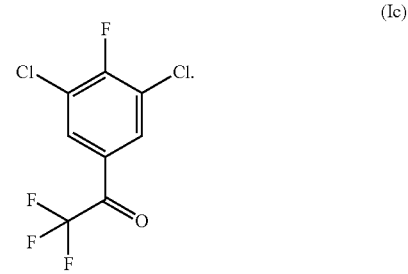 [SMILES: O=C(c1cc(Cl)c(F)c(Cl)c1)C(F)(F)F]

(Ic)

In a 250 mL 3-neck round-bottom flask equipped with a magnetic stirrer, a thermometer, a glass pipe for gas introduction and a reflux condenser, was placed the compound of formula IVc (1-(3-chloro-4-fluoro-5-nitro-phenyl)-2,2,2-trifluoro-ethanone, 204.0 g, 0.687 mol, 91.5% purity) and anhydrous calcium chloride (3.9 g). The flask was placed in a sand bath and heated to 210° C. (internal temperature). A slow stream of chlorine gas (about 1.5 g/h) was introduced under the liquid surface over a period of 33 h. During this time the reaction temperature was gradually reduced from 210° C. to 183° C. Reaction off-gas was scrubbed in a 10% sodium hydroxide solution. At this time, the conversion of the starting material was 96% according to $^1$H NMR analysis. The reaction mixture was cooled to ambient temperature and discharged. The crude reaction mixture was fractionated under reduce pressure (93 mbar) using a 30 cm distillation column (evacuated, silver coated insulating jacket, packed with glass beds) to give the title compound of formula Ic (b.p. 100-102° C., 142 g). The title compound of formula Ic had a purity of 95% according to the quantitative GC analysis.

The invention claimed is:

1. A process for the preparation of a compound of Formula I:

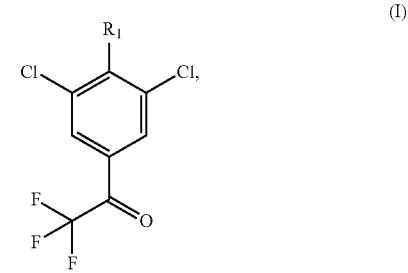

(I)

wherein

R₁ is hydrogen, fluoro or chloro; which process comprises a) reacting a compound of Formula II:

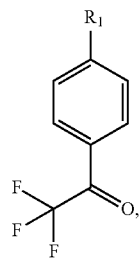

(II)

wherein R₁ is hydrogen, fluoro or chloro; with a nitration agent to the compound of Formula III:

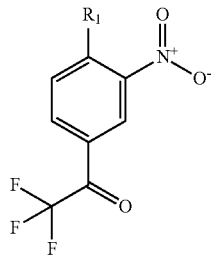

(III)

wherein R₁ is hydrogen, fluoro or chloro;

b) reacting the compound of Formula III with trichloroisocyanuric acid in the presence of sulfuric acid or fuming sulfuric acid to the compound of Formula IV:

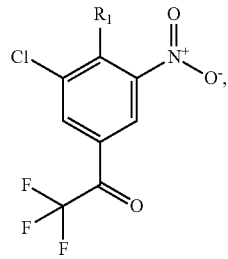

(IV)

wherein R₁ is hydrogen, fluoro or chloro; and c) reacting the compound of Formula IV with chlorine gas at a temperature from 180° C. to 250° C. to the compound of Formula I.

2. The process according to claim 1, characterized in that the nitration agent is selected from sulfuric acid, nitric acid and their salts.

3. The process according to claim 1, characterized in that the process is performed without isolating the intermediate of Formula III.

4. A process for the preparation of a compound of Formula II:

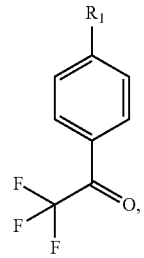

(II)

wherein R₁ is fluoro; characterized in that fluorobenzene is reacted with trifluoroacetyl chloride in the presence of aluminium chloride.

* * * * *